United States Patent
McGee (10) Patent No.: US 9,241,687 B2
(45) Date of Patent: *Jan. 26, 2016

(54) ABLATION PROBE WITH ULTRASONIC IMAGING CAPABILITIES

(75) Inventor: David L. McGee, Sunnyvale, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 534 days.

This patent is subject to a terminal disclaimer.

(21) Appl. No.: 13/437,267

(22) Filed: Apr. 2, 2012

(65) Prior Publication Data

US 2012/0310064 A1    Dec. 6, 2012

Related U.S. Application Data

(60) Provisional application No. 61/491,944, filed on Jun. 1, 2011.

(51) Int. Cl.

| | | |
|---|---|---|
| *A61B 18/14* | (2006.01) | |
| *A61B 8/00* | (2006.01) | |
| *A61B 8/08* | (2006.01) | |
| *A61B 8/12* | (2006.01) | |
| A61B 6/12 | (2006.01) | |
| A61B 6/00 | (2006.01) | |

(52) U.S. Cl.
CPC ............. *A61B 8/4477* (2013.01); *A61B 8/0883* (2013.01); *A61B 8/12* (2013.01); *A61B 8/445* (2013.01); *A61B 8/463* (2013.01); *A61B 6/12* (2013.01); *A61B 6/487* (2013.01)

(58) Field of Classification Search
CPC ............... A61B 8/445; A61B 18/1492; A61B 2017/00022; A61B 2017/00106; A61B 2018/00577; A61B 2019/5276; A61B 2019/5278; A61B 2019/5285
USPC ................................. 606/32–34, 41
See application file for complete search history.

(56) References Cited

U.S. PATENT DOCUMENTS

| | | |
|---|---|---|
| 3,773,401 A | 11/1973 | Douklias et al. |
| 4,763,660 A | 8/1988 | Kroll et al. |
| 5,029,588 A | 7/1991 | Yock et al. |
| 5,240,003 A | 8/1993 | Lancee et al. |

(Continued)

FOREIGN PATENT DOCUMENTS

| | | |
|---|---|---|
| CN | 104619259 A | 5/2015 |
| EP | 1343426 B1 | 9/2003 |

(Continued)

OTHER PUBLICATIONS

International Search Report and Written Opinion issued in PCT/US2012/031819, mailed Sep. 27, 2012, 16 pages.

(Continued)

*Primary Examiner* — Allen Porter, Jr.
(74) *Attorney, Agent, or Firm* — Faegre Baker Daniels LLP (57) ABSTRACT

Devices and systems for ultrasonically imaging anatomical structures and performing ablation therapy within the body are disclosed. A combined ablation and ultrasound imaging probe includes a housing, an ablation electrode located on a distal tip section of the housing, and a number of ultrasonic imaging sensors configured for visualizing anatomical structures within the body. During an ablation procedure, the ultrasonic imaging sensors can be tasked to generate a number of ultrasonic images that can be displayed as a composite image on a display screen of a user interface.

18 Claims, 6 Drawing Sheets

(56) References Cited

U.S. PATENT DOCUMENTS

| | | |
|---|---|---|
| 5,254,088 A | 10/1993 | Lundquist et al. |
| 5,331,966 A | 7/1994 | Bennett et al. |
| 5,383,874 A | 1/1995 | Jackson et al. |
| 5,385,146 A | 1/1995 | Goldreyer |
| 5,385,148 A | 1/1995 | Lesh et al. |
| 5,391,199 A | 2/1995 | Ben-Haim |
| 5,398,683 A | 3/1995 | Edwards et al. |
| 5,462,521 A | 10/1995 | Brucker et al. |
| 5,485,849 A | 1/1996 | Panescu et al. |
| 5,494,042 A | 2/1996 | Panescu et al. |
| 5,500,012 A | 3/1996 | Brucker et al. |
| 5,571,088 A | 11/1996 | Lennox et al. |
| 5,579,764 A | 12/1996 | Goldreyer |
| 5,582,609 A | 12/1996 | Swanson et al. |
| 5,647,870 A | 7/1997 | Kordis et al. |
| 5,762,067 A | 6/1998 | Dunham et al. |
| 5,788,636 A | 8/1998 | Curley |
| 5,800,482 A | 9/1998 | Pomeranz et al. |
| 5,830,213 A | 11/1998 | Panescu et al. |
| 5,833,621 A | 11/1998 | Panescu et al. |
| 5,868,735 A | 2/1999 | Lafontaine |
| 5,871,483 A | 2/1999 | Jackson et al. |
| 6,004,269 A | 12/1999 | Crowley et al. |
| 6,050,994 A | 4/2000 | Sherman |
| 6,059,778 A | 5/2000 | Sherman |
| 6,064,905 A | 5/2000 | Webster, Jr. et al. |
| 6,070,094 A | 5/2000 | Swanson et al. |
| 6,083,170 A | 7/2000 | Ben-Haim |
| 6,101,409 A | 8/2000 | Swanson et al. |
| 6,116,027 A | 9/2000 | Smith et al. |
| 6,165,123 A | 12/2000 | Thompson |
| 6,171,305 B1 | 1/2001 | Sherman |
| 6,200,314 B1 | 3/2001 | Sherman |
| 6,210,337 B1 | 4/2001 | Dunham et al. |
| 6,233,491 B1 | 5/2001 | Kordis et al. |
| 6,241,754 B1 | 6/2001 | Swanson et al. |
| 6,290,697 B1 | 9/2001 | Tu et al. |
| 6,352,534 B1 | 3/2002 | Paddock et al. |
| 6,423,002 B1 | 7/2002 | Hossack |
| 6,475,213 B1 | 11/2002 | Whayne et al. |
| 6,488,678 B2 | 12/2002 | Sherman |
| 6,491,710 B2 | 12/2002 | Satake |
| 6,508,767 B2 | 1/2003 | Burns et al. |
| 6,508,769 B2 | 1/2003 | Bonnefous |
| 6,516,667 B1 | 2/2003 | Broad et al. |
| 6,517,533 B1 | 2/2003 | Swaminathan |
| 6,537,271 B1 | 3/2003 | Murray et al. |
| 6,544,175 B1 | 4/2003 | Newman |
| 6,547,788 B1 | 4/2003 | Maguire et al. |
| 6,572,549 B1 | 6/2003 | Jong et al. |
| 6,575,966 B2 | 6/2003 | Lane et al. |
| 6,579,278 B1 | 6/2003 | Bencini |
| 6,582,372 B2 | 6/2003 | Poland |
| 6,589,182 B1 | 7/2003 | Loftman et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |
| 6,640,120 B1 | 10/2003 | Swanson et al. |
| 6,656,174 B1 | 12/2003 | Hegde et al. |
| 6,658,279 B2 | 12/2003 | Swanson et al. |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,735,465 B2 | 5/2004 | Panescu |
| 6,736,814 B2 | 5/2004 | Manna et al. |
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,811,550 B2 | 11/2004 | Holland et al. |
| 6,824,517 B2 | 11/2004 | Salgo et al. |
| 6,837,884 B2 | 1/2005 | Woloszko |
| 6,917,834 B2 | 7/2005 | Koblish et al. |
| 6,922,579 B2 | 7/2005 | Taimisto et al. |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,105,122 B2 | 9/2006 | Karason |
| 7,112,198 B2 | 9/2006 | Satake |
| 7,115,122 B1 | 10/2006 | Swanson et al. |
| 7,131,947 B2 | 11/2006 | Demers |
| 7,166,075 B2 | 1/2007 | Varghese et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D'Sa |
| 7,347,820 B2 | 3/2008 | Bonnefous |
| 7,347,821 B2 | 3/2008 | Dkyba et al. |
| 7,347,857 B2 | 3/2008 | Anderson et al. |
| 7,361,144 B2 | 4/2008 | Levrier et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,892,228 B2 | 2/2011 | Landis et al. |
| 7,918,850 B2 | 4/2011 | Govari et al. |
| 8,016,822 B2 | 9/2011 | Swanson |
| 8,740,900 B2 | 6/2014 | Kim et al. |
| 2002/0087208 A1 | 7/2002 | Koblish et al. |
| 2003/0013958 A1 | 1/2003 | Govari et al. |
| 2003/0088240 A1 | 5/2003 | Saadat |
| 2003/0158548 A1 | 8/2003 | Phan et al. |
| 2003/0158549 A1 | 8/2003 | Swanson |
| 2003/0229286 A1 | 12/2003 | Lenker |
| 2004/0147920 A1 | 7/2004 | Keidar |
| 2004/0162556 A1 | 8/2004 | Saadat |
| 2004/0186467 A1 | 9/2004 | Swanson et al. |
| 2004/0215177 A1 | 10/2004 | Swanson |
| 2004/0215186 A1 | 10/2004 | Cornelius et al. |
| 2005/0033331 A1 | 2/2005 | Burnett et al. |
| 2005/0059862 A1 | 3/2005 | Phan |

(56) References Cited

U.S. PATENT DOCUMENTS

| | | |
|---|---|---|
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0187544 A1 | 8/2005 | Swanson et al. |
| 2005/0228286 A1 | 10/2005 | Messerly et al. |
| 2005/0228504 A1 | 10/2005 | Demarais |
| 2005/0273060 A1 | 12/2005 | Levy et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0247607 A1 | 11/2006 | Cornelius et al. |
| 2006/0253028 A1 | 11/2006 | Lam et al. |
| 2006/0253116 A1 | 11/2006 | Avitall et al. |
| 2007/0003811 A1 | 1/2007 | Zerfass et al. |
| 2007/0016054 A1 | 1/2007 | Yuan et al. |
| 2007/0016059 A1 | 1/2007 | Morimoto et al. |
| 2007/0016228 A1 | 1/2007 | Salas |
| 2007/0021744 A1* | 1/2007 | Creighton IV .......... 606/32 |
| 2007/0049925 A1 | 3/2007 | Phan et al. |
| 2007/0073135 A1 | 3/2007 | Lee et al. |
| 2007/0088345 A1 | 4/2007 | Larson et al. |
| 2007/0167813 A1 | 7/2007 | Lee et al. |
| 2007/0270794 A1 | 11/2007 | Anderson et al. |
| 2008/0009733 A1 | 1/2008 | Saksena |
| 2008/0025145 A1 | 1/2008 | Peszynski et al. |
| 2008/0058836 A1 | 3/2008 | Moll et al. |
| 2008/0091109 A1 | 4/2008 | Abraham |
| 2008/0140065 A1 | 6/2008 | Rioux et al. |
| 2008/0161795 A1 | 7/2008 | Wang et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0275428 A1 | 11/2008 | Tegg et al. |
| 2008/0281322 A1 | 11/2008 | Sherman et al. |
| 2008/0287803 A1 | 11/2008 | Li et al. |
| 2009/0030312 A1 | 1/2009 | Hadjicostis |
| 2009/0048591 A1 | 2/2009 | Ibrahim et al. |
| 2009/0062790 A1 | 3/2009 | Malchano et al. |
| 2009/0076390 A1 | 3/2009 | Lee et al. |
| 2009/0093810 A1 | 4/2009 | Subramaniam et al. |
| 2009/0093811 A1 | 4/2009 | Koblish et al. |
| 2009/0182316 A1 | 7/2009 | Bencini |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0287202 A1 | 11/2009 | Ingle et al. |
| 2009/0292209 A1 | 11/2009 | Hadjicostis |
| 2009/0299360 A1 | 12/2009 | Ormsby |
| 2010/0010487 A1 | 1/2010 | Phan et al. |
| 2010/0057072 A1 | 3/2010 | Roman et al. |
| 2010/0106155 A1 | 4/2010 | Anderson et al. |
| 2010/0113938 A1 | 5/2010 | Park et al. |
| 2010/0168568 A1 | 7/2010 | Sliwa |
| 2010/0168570 A1 | 7/2010 | Sliwa et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0331658 A1 | 12/2010 | Kim et al. |
| 2011/0071400 A1 | 3/2011 | Hastings et al. |
| 2011/0071401 A1 | 3/2011 | Hastings et al. |
| 2011/0125143 A1 | 5/2011 | Gross et al. |
| 2011/0130648 A1 | 6/2011 | Beeckler et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2012/0095347 A1 | 4/2012 | Adam et al. |
| 2012/0136351 A1 | 5/2012 | Weekamp et al. |
| 2012/0172698 A1 | 7/2012 | Hastings et al. |
| 2012/0172727 A1 | 7/2012 | Hastings et al. |
| 2012/0172871 A1 | 7/2012 | Hastings et al. |
| 2012/0330304 A1 | 12/2012 | Vegesna et al. |
| 2013/0023897 A1 | 1/2013 | Wallace |
| 2013/0066312 A1 | 3/2013 | Subramaniam et al. |
| 2013/0066315 A1 | 3/2013 | Subramaniam et al. |
| 2013/0172742 A1 | 7/2013 | Rankin et al. |
| 2013/0197363 A1 | 8/2013 | Rankin et al. |
| 2014/0066764 A1 | 3/2014 | Subramaniam et al. |
| 2014/0081262 A1 | 3/2014 | Koblish et al. |
| 2014/0276052 A1 | 9/2014 | Rankin et al. |

FOREIGN PATENT DOCUMENTS

| | | |
|---|---|---|
| EP | 1343427 B1 | 9/2003 |
| EP | 1547537 A1 | 6/2005 |
| EP | 1717601 A2 | 11/2006 |
| EP | 1935332 A2 | 6/2008 |
| JP | 2000000242 A | 1/2000 |
| JP | 2006239414 A | 9/2006 |
| JP | 2007163559 A | 6/2007 |
| JP | 2007244857 A | 9/2007 |
| JP | 2009142653 A | 12/2008 |
| JP | 2010522623 A | 7/2010 |
| JP | 2015509027 A | 4/2012 |
| WO | WO9927862 A1 | 6/1999 |
| WO | WO0029062 A2 | 5/2000 |
| WO | WO0164145 A1 | 9/2001 |
| WO | WO0168173 A2 | 9/2001 |
| WO | WO0205868 A2 | 1/2002 |
| WO | WO0209599 A2 | 2/2002 |
| WO | WO0219934 A1 | 3/2002 |
| WO | WO02102234 A2 | 12/2002 |
| WO | WO03039338 A2 | 5/2003 |
| WO | WO2007079278 A1 | 7/2007 |
| WO | WO2008046031 A2 | 4/2008 |
| WO | WO2009032421 A2 | 3/2009 |
| WO | 2010082146 A1 | 7/2010 |
| WO | 2011033421 A1 | 3/2011 |
| WO | WO2011024133 A1 | 3/2011 |
| WO | WO2011089537 A1 | 7/2011 |
| WO | 2011101778 A1 | 8/2011 |
| WO | WO2011095937 A1 | 8/2011 |
| WO | 2012001595 A1 | 1/2012 |
| WO | WO2012001595 A1 | 1/2012 |
| WO | WO2012049621 A1 | 4/2012 |
| WO | WO2012066430 A1 | 5/2012 |

OTHER PUBLICATIONS

International Search Report and Written Opinion issued in PCT/US2013/058105, mailed Nov. 22, 2013, 16 pages.

International Search Report and Written Opinion issued in PCT/US2013/060612, mailed Feb. 28, 2014, 16 pages.

Invitation to Pay Additional Fees and Partial International Search Report issued in PCT/US2014/027491, mailed Jul. 28, 2014, 5 pages.

Goldberg, S. Nahum et al., "Variables Affecting Proper System Grounding for Radiofrequency Ablation in an Animal Model", JVIR, vol. 11, No. 8, Sep. 2000, pp. 1069-1075.

International Search Report and Written Opinion issued in PCT/US2008/058324, dated Aug. 18, 2008, 11 pages.

Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.

Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.

Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.

International Search Report and Written Opinion issued in PCT/US2012/055309, mailed Nov. 19, 2012, 13 pages.

International Search Report and Written Opinion issued in PCT/US2012/072061, mailed Mar. 21, 2013, 9 pages.

(56) References Cited

OTHER PUBLICATIONS

International Search Report and Written Opinion issued in PCT/US2013/020503, mailed Mar. 20, 2013, 10 pages.
Partial International Search Report issued in PCT/US2012/0551545, mailed Dec. 20, 2012, 7 pages.
International Search Report and Written Opinion issued in PCT/US2014/027491, mailed Sep. 23, 2014, 17 pages.
International Preliminary Report on Patentability issued in PCT/US2013/058105, completed Mar. 10, 2015.
International Preliminary Report on Patentability issued in PCT/US2014/027491, mailed Sep. 24, 2015, 12 pages.

* cited by examiner

ABLATION PROBE WITH ULTRASONIC IMAGING CAPABILITIES

CROSS REFERENCE TO RELATED APPLICATION

This application claims priority to U.S. Provisional Application No. 61/491,944, filed Jun. 1, 2011, and entitled "ABLATION PROBE WITH ULTRASONIC IMAGING CAPABILITIES," which is incorporated herein by reference in its entirety for all purposes.

TECHNICAL FIELD

The present disclosure relates generally to devices and systems for imaging anatomical structures within the body. More specifically, the present disclosure relates to an ablation probe with ultrasonic imaging capabilities.

BACKGROUND

In ablation therapy, it is often necessary to determine various characteristics of body tissue at a target ablation site within the body. In interventional cardiac electrophysiology (EP) procedures, for example, it is often necessary for the physician to determine the condition of cardiac tissue at a target ablation site in or near the heart. During some EP procedures, the physician may deliver a mapping catheter through a main vein or artery into an interior region of the heart to be treated. Using the mapping catheter, the physician may then determine the source of a cardiac rhythm disturbance or abnormality by placing a number of mapping elements carried by the catheter into contact with the adjacent cardiac tissue and then operate the catheter to generate an electrophysiology map of the interior region of the heart. Once a map of the heart is generated, the physician may then advance an ablation catheter into the heart, and position an ablation electrode carried by the catheter tip near the targeted cardiac tissue to ablate the tissue and form a lesion, thereby treating the cardiac rhythm disturbance or abnormality. In some techniques, the ablation catheter itself may include a number of mapping electrodes, allowing the same device to be used for both mapping and ablation.

Various ultrasound-based imaging catheters and probes have been developed for directly visualizing body tissue in applications such as interventional cardiology, interventional radiology, and electrophysiology. For interventional cardiac electrophysiology procedures, for example, ultrasound imaging devices have been developed that permit the visualization of anatomical structures of the heart directly and in real-time. In some electrophysiology procedures, for example, ultrasound catheters may be used to image the intra-atrial septum, to guide transseptal crossing of the atrial septum, to locate and image the pulmonary veins, and to monitor the atrial chambers of the heart for signs of a perforation and pericardial effusion.

Many ultrasound-based imaging systems comprise an imaging probe that is separate from the mapping and ablation catheters used to perform therapy on the patient. As a result, a position tracking system is sometimes used to track the location of each device within the body. In some procedures, it may be difficult for the physician to quickly and accurately determine the condition of tissue to be ablated. Moreover, the images obtained using many ultrasound-based imaging systems are often difficult to read and understand without reference to images obtained from a separate imaging system such as a fluoroscopic imaging system.

SUMMARY

The present disclosure relates to devices and systems for imaging an ablation probe within the body. In Example 1, a combined ablation and ultrasound imaging probe for insertion within a body comprises: a housing having a proximal section and a distal tip section; an ablation electrode located at the distal tip section; a first ultrasonic imaging sensor located on the distal tip section, the first ultrasonic imaging sensor configured to transmit acoustic waves in a first direction distal to the distal tip section; and a plurality of second ultrasonic imaging sensors located on the distal tip section proximal to the first ultrasonic imaging sensor, each of the second ultrasonic imaging sensors configured to transmit an acoustic wave in a second direction different from the first direction.

In Example 2, the probe according to Example 1, wherein the ablation electrode comprises an RF ablation electrode.

In Example 3, the probe according to any of Examples 1-2, wherein each of the first and second ultrasonic imaging sensors are disposed within the distal tip section.

In Example 4, the probe according to any of Examples 1-3, wherein the first ultrasonic imaging sensor comprises a distal-facing ultrasonic imaging sensor located at a distal end of the distal tip section.

In Example 5, the probe according to any of Examples 1-4, wherein each of the second ultrasonic imaging sensors are coupled to a curved portion of the distal tip section.

In Example 6, the probe according to Example 5, wherein each of the second ultrasonic imaging sensors are configured to transmit acoustic waves at an angle of between about 10° to about 60° relative to a line perpendicular to a longitudinal axis of the housing.

In Example 7, the probe according to any of Examples 1-6, wherein the second ultrasonic imaging sensors are radially disposed about a circumference of the distal tip section.

In Example 8, the probe according to Example 7, wherein the second ultrasonic imaging sensors are radially spaced at equidistant intervals from each other about the circumference.

In Example 9, the probe according to any of Examples 1-8, wherein the probe further includes at least one mapping electrode.

In Example 10, an ablation and ultrasound imaging system comprises: a probe including a housing with a proximal section and a distal tip section, an ablation electrode, and a plurality of ultrasonic imaging sensors; the plurality of ultrasonic imaging sensors including a first ultrasonic imaging sensor located on the distal tip section and a plurality of second ultrasonic imaging sensors located on the distal tip section proximal to the first ultrasonic imaging sensor; an ablation therapy module configured for generating and supplying an electrical signal to the ablation electrode; an ultrasound imaging module configured for processing ultrasonic imaging signals received from the ultrasonic imaging sensors; and a user interface configured for displaying ultrasonically derived information generated by the ultrasonic imaging sensors on a display screen.

In Example 11, the system according to Example 10, wherein the first ultrasonic imaging sensor comprises a distal-facing ultrasonic imaging sensor disposed at a distal end of the distal tip section.

In Example 12, the system according to any of Examples 10-12, wherein each of the second ultrasonic imaging sensors are coupled to a curved portion of the distal tip section.

In Example 13, the system according to any of Examples 10-12, wherein the ultrasonic imaging module comprises: an imaging controller including an ultrasonic signal generator configured to generate control signals for controlling each ultrasonic imaging sensor; and an image processor configured for processing electrical signals received from each ultrasonic imaging sensor and generating a plurality of ultrasonic images.

In Example 14, the system according to any of Examples 10-13, further comprising a mapping processor in communication with one or more mapping electrodes on the probe.

In Example 15, the system according to any of Examples 10-14, wherein the display screen includes a plurality of imaging panes each configured for displaying an image associated with an associated ultrasonic imaging sensor.

In Example 16, the system according to Example 15, wherein the plurality of imaging panes are displayed in a side-by-side configuration on the display screen.

In Example 17, the system according to Example 15, wherein each imaging pane includes a B-mode ultrasonic image.

In Example 18, a user interface for displaying a composite image generated from an ablation probe with multiple ultrasonic imaging sensors comprises: a display screen including a plurality of imaging panes each configured to display an ultrasonic image generated from an associated one of the ultrasonic imaging sensors; wherein each of the imaging panes are arranged side-by-side to form a composite ultrasonic image from each of the ultrasonic imaging sensors.

In Example 19, the user interface according to Example 18, wherein the ultrasonic images are B-mode images.

In Example 20, the user interface according to any of Examples 18-19, wherein the display screen includes a set of reference numbers indicating an imaging depth of the images generated by each ultrasonic imaging sensor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
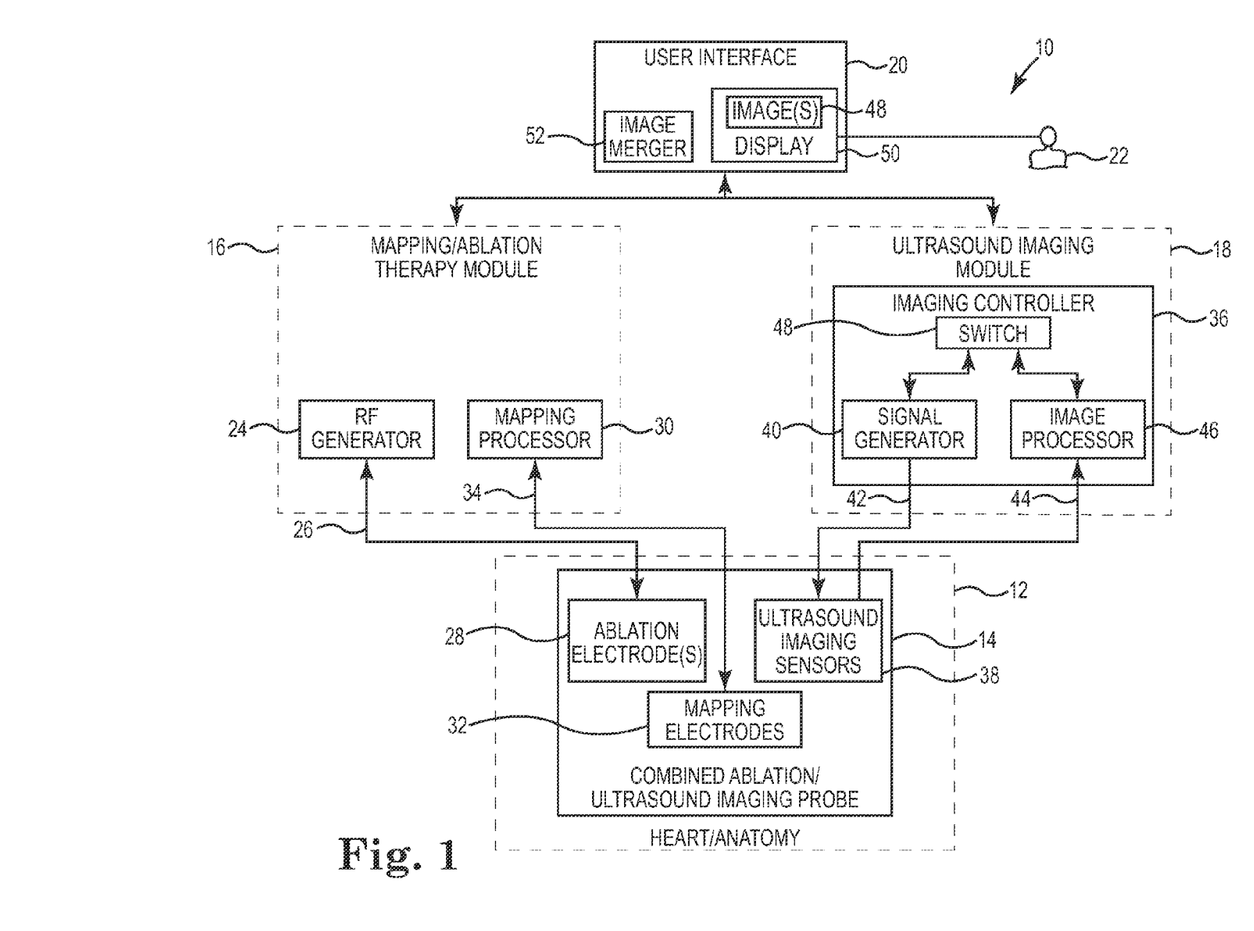
FIG. 1 is a functional block diagram showing a medical system in accordance with an illustrative embodiment.

FIG. 1 is a functional block diagram showing a medical system 10 in accordance with an illustrative embodiment. The system 10, illustratively an ultrasonic cardiac imaging system for imaging the treatment of a heart 12, includes a combined ablation and ultrasonic imaging probe 14, a therapy module 16 for mapping and treating the heart 12, an ultrasound imaging module 18 for generating high resolution ultrasonic images (e.g., B-mode images) of anatomical structures (e.g., body tissue) in or near the heart 12, and a user interface 20 configured for use by the physician 22 in controlling therapy provided by the probe 14, visualizing anatomical structures and/or other devices within the body, and/or determining the location and orientation of the probe 14 within the body. In some embodiments, for example, the system 10 comprises an ultrasonic imaging system that can be used in monitoring RF ablation therapy provided to a patient's heart 12 or in a cardiac vessel leading into or from the heart 12.

The therapy module 16 is used for identifying and treating a target tissue site or multiple sites within the body such as an aberrant conductive pathway. In the embodiment of FIG. 1, the therapy module 16 comprises a radio frequency (RF) generator 24 that supplies an RF signal 26 to one or more ablation electrodes 28 located on a distal tip of the probe, and a mapping processor 30 that can be used to identify one or more potential therapeutic sites in or near the heart 12. The RF generator 24 is configured to deliver ablation energy to each ablation electrode 28 in a controlled manner to ablate any sites identified by the mapping processor 30. Other types of ablation sources in addition to or in lieu of the RF generator 24 can also be used for ablating target sites. Examples of other types of ablation sources can include, but are not limited to, microwave generators, acoustic generators, cryoablation generators, and laser/optical generators.

In some embodiments, the probe 14 further includes one or more mapping electrodes 32 coupled to the mapping processor 30. During operation, the mapping processor 30 detects and analyzes electrical signals within the myocardial tissue in order to identify potential treatment sites for ablation using the probe 14. In some embodiments, the ablation electrode 28 or multiple ablation electrodes 28 can be used for performing both mapping and ablation functions. In other embodiments, the electrode 28 is a dedicated ablation electrode, and one or more separate electrodes 32 on the probe 14 can be tasked to perform mapping functions. In other embodiments, a separate mapping catheter is used to map potential ablation sites within the body.

The mapping processor 30 is configured to derive activation times and voltage distribution from the electrical signals 34 obtained from each mapping electrode 32 to determine the presence of irregular electrical activity within the heart 12, which can then be graphically displayed as a map on the user interface 20. Further details regarding electrophysiology mapping are provided, for example, in U.S. Pat. Nos. 5,485,849, 5,494,042, 5,833,621, and 6,101,409, each of which are expressly incorporated herein by reference in their entirety for all purposes.

In the embodiment of FIG. 1, the ultrasound imaging module 18 includes an imaging controller 36 coupled to a number of ultrasonic imaging sensors 38 on the probe 14. An ultrasonic signal generator 40 is configured to provide one or more control signals 42 for controlling each of the ultrasonic sensors 38. The imaging signals 44 received back from the ultrasonic sensors 38, in turn, are fed to an image processor 46, which processes the electrical signals 44 received back from the ultrasonic sensors 38 and generates a number of images, which as is discussed further herein, can be assembled together and displayed as a composite image on the user interface 20 to assist the physician 22 with inserting the probe 14 into position at a target location within the body and to perform an ablation procedure. In some embodiments, for example, the ultrasonic images obtained via the ultrasound imaging module 18 can be used to confirm tissue contact of the probe 14 with the heart 12 or surrounding anatomy, to determine the orientation of the probe 14 within the body, to determine the tissue depth of the tissue at a target ablation site, and/or to visualize the progression of a lesion being formed in the tissue.

The imaging controller 36 is configured to control the ultrasonic sensors 38 to generate ultrasonic images using a pulse-echo imaging technique, in which ultrasonic waves are transmitted by the ultrasonic sensors 38 in a transmit mode into the surrounding body, and the reflected waves are sensed by the ultrasonic sensors 38 operating in a receive mode. In some embodiments, the control signals 42 used for generating ultrasonic waves are applied to each of the ultrasonic sensors 38 simultaneously. Alternatively, and in other embodiments, a switching element 48 such as a microswitch or MUX can be controlled to selectively activate only a subset of the ultrasonic sensors 38. In one embodiment, for example, the ultrasound controller 30 can control the switching element 48 to selectively activate each individual ultrasonic sensor 38 in a sequence or pattern. During imaging, the sequential activation of each ultrasonic sensor 38 may help to reduce or prevent interference with the reflected ultrasonic waves received from other sensors 38, which helps to reduce cross-talk or other undesired artifacts in the imaging signal 44. In some embodiments, the sequential activation of the ultrasonic sensors 38 may permit the field of view of the ultrasonic sensors 38 to be overlapped slightly without causing interference in the imaging signals 44.

Various characteristics associated with the ultrasonic sensors 38 as well as the circuitry within the ultrasound imaging module 18 can be controlled to optimize the suitability of the ultrasonic sensors 38 to accurately detect tissue boundaries (e.g., blood or other bodily fluid), lesion formation and progression, as well as other characteristics of the tissue before, during, and/or after the ablation procedure. Example tissue characteristics that can be visualized using the probe 14 include, but are not limited to, the presence of fluid vaporization inside the tissue, the existence of a prior scar, and the size and shape of a lesion being formed. The depth at which the ultrasonic sensors 38 can visualize anatomical structures within the body is dependent on the mechanical characteristics of the elements 38, the electrical characteristics of the transducer circuitry including the drive frequency of the control signal 42 provided by the signal generator 40, the boundary conditions and degree of attenuation between the ultrasonic sensors 38 and the surrounding anatomy, as well as other factors.

The imaging signals 44 sensed by each ultrasonic sensor 38 are fed to the imaging processor 46, which generates ultrasonically derived information that can be displayed on a display monitor 50 of the user interface 20. In some embodiments, the imaging processor 46 uses the imaging signals 44 to produce a number of images 48 on the display monitor 50. Other ultrasonically derived information can also be displayed on the display monitor 50 in conjunction with, or in lieu of, the images 48.

In some embodiments, an image merger 52 is configured to superimpose graphical information obtained from the imaging module 18 and superimpose that information on the display monitor 50 along with graphical information acquired from other sources (e.g., a fluoroscopic monitor) and/or position information from the therapy module 16 to form a composite medical image. In some embodiments, the imaging processor 46 may further superimpose colors, labels, and/or other artifacts onto the images 48 for identifying features within the images. For example, and in some embodiments, the imaging processor 46 may superimpose a first color (e.g., green) onto the images 48 to indicate the location where the distal tip section 60 of the probe 14 is near or in contact with the body tissue to be ablated and a second color (e.g., red) to indicate body tissue located further away from the distal tip section 60. In other embodiments, flashing colors or other features on the display monitor 50 may utilized for qualitatively and/or quantitatively assessing contact with the body tissue.

Figure 6:
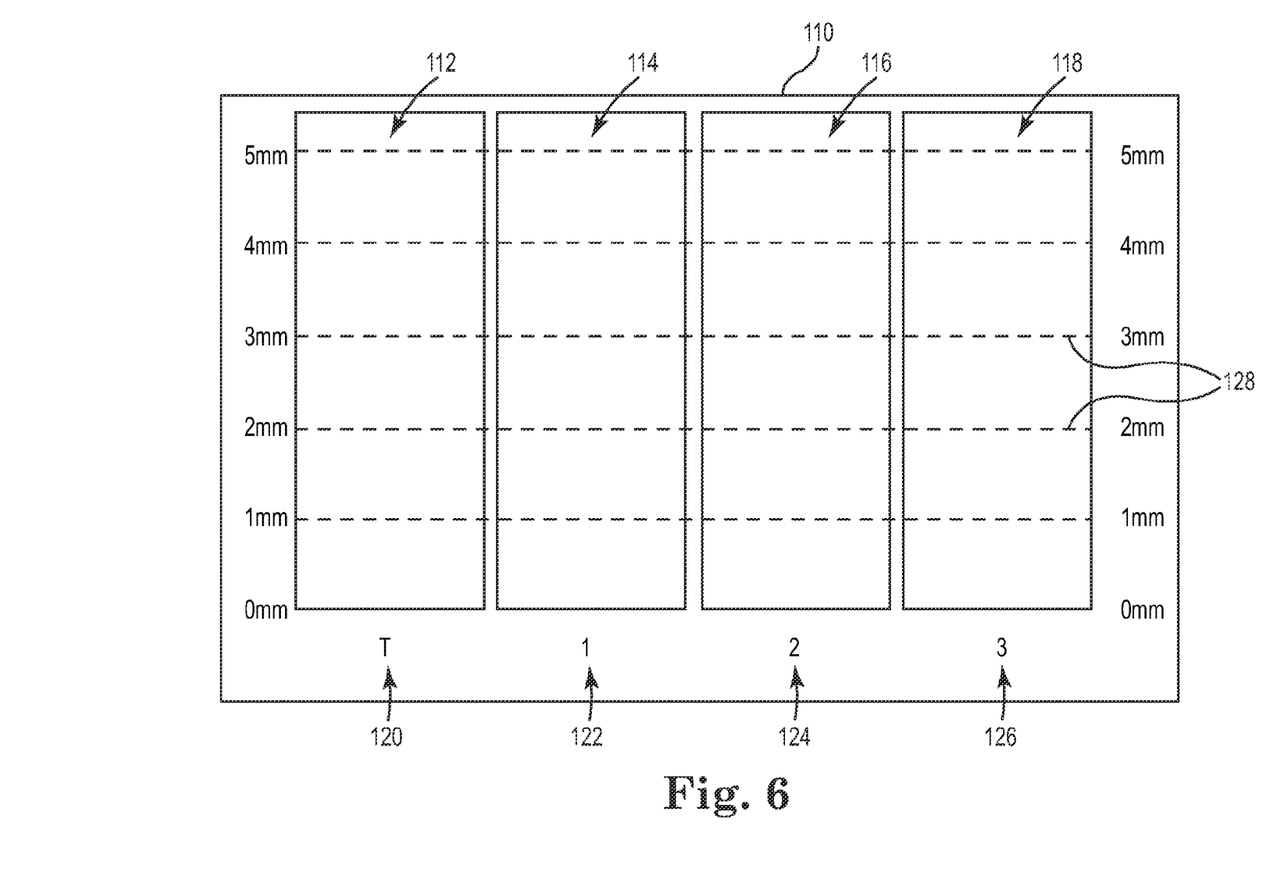
FIG. 6 is a view showing an example display screen that can be used to display ultrasonic images generated using the ultrasonic imaging probe of FIG. 2.
Figure 7:
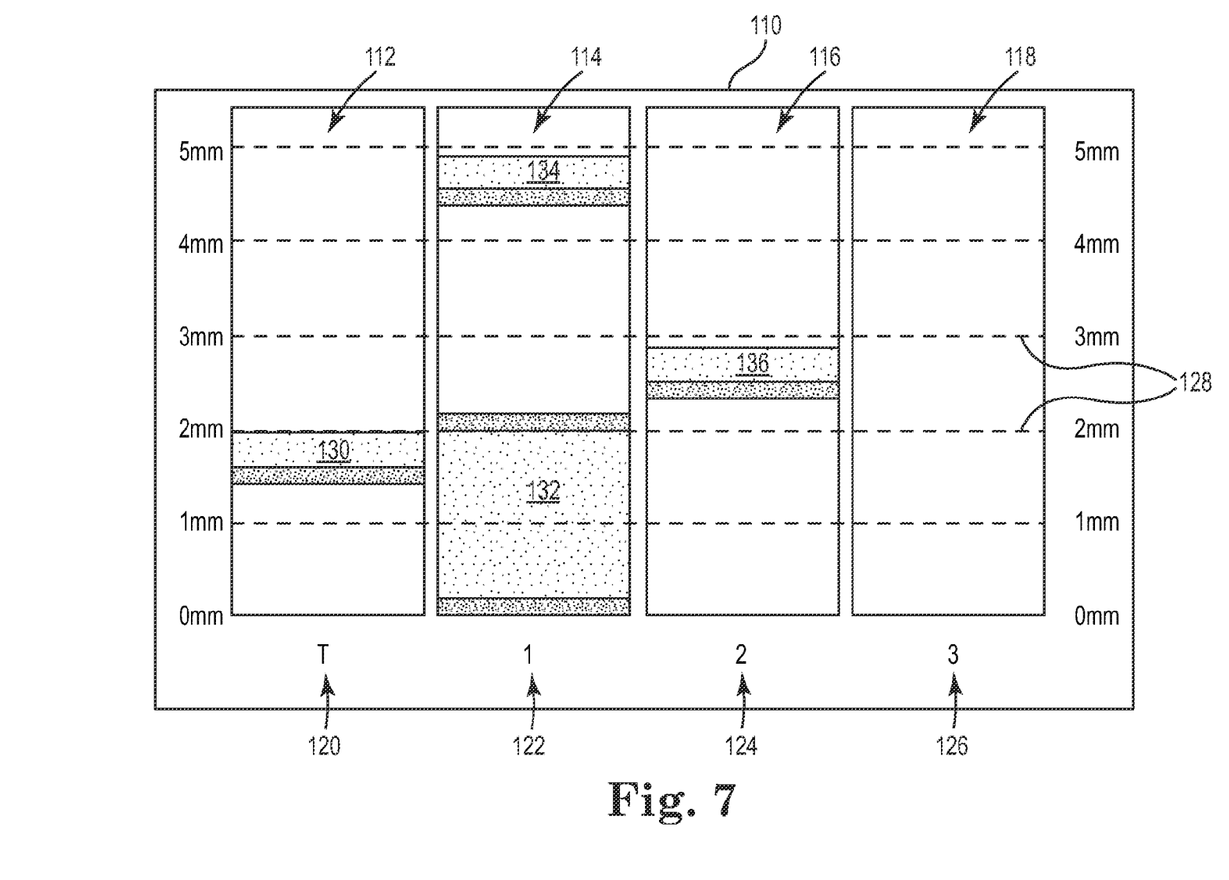
FIG. 7 is a view showing a number of ultrasonic images generated on the display screen of FIG. 6.

In one embodiment described further with respect to FIGS. 6-7, the images received from each sensor 38 as well as other ultrasonically derived information can be arranged side-by-side on the display monitor 50, allowing the physician to quickly assess factors such as the contact site, tip/tissue orientation, lesion formation and progression, and tissue wall thickness (e.g., in thin-walled anatomical structures). The image 48 could be displayed, for example, on an existing monitor in an EP lab, on a dedicated display monitor, or simultaneously at multiple locations.

Although the system 10 is described in the context of a medical system for use in intracardiac electrophysiology procedures for diagnosing and treating the heart, in other embodiments the system 10 may be used for treating, diagnosing, or otherwise visualizing other anatomical structures such as the prostate, brain, gall bladder, uterus, esophagus, and/or other regions in the body. Moreover, many of the elements in FIG. 1 are functional in nature, and are not meant to limit the structure that performs these functions in any manner. For example, several of the functional blocks can be embodied in a single device, or one or more of the functional blocks can be embodied in multiple devices.

Figure 2:
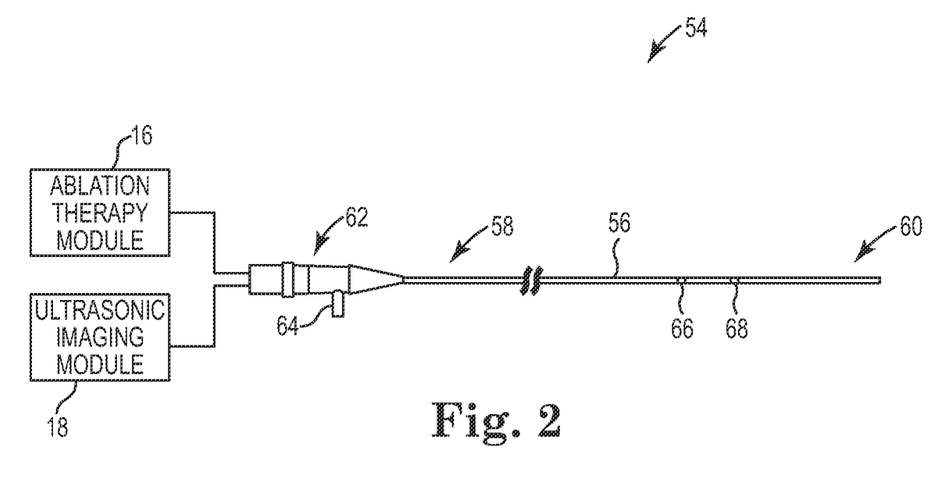
FIG. 2 is a schematic view showing a combined ablation and ultrasonic imaging probe in accordance with an illustrative embodiment.

FIG. 2 is a schematic view showing a combined ablation and ultrasonic imaging probe 54 in accordance with an illustrative embodiment for use with the system 10 of FIG. 1. In the embodiment of FIG. 2, the probe 54 comprises a catheter body including an elongate tubular housing 56 having a proximal section 58 and a distal tip section 60. The proximal section 58 of the housing 56 is coupled to a proximal hub 62, which includes a fluid port 64 for providing acoustic coupling/cooling fluid to the distal tip section 60 of the probe 54. The proximal hub 62 is electrically connected to both the therapy module 16 and the ultrasonic imaging module 18, as shown.

In the embodiment of FIG. 2, the probe 54 includes one or more dedicated mapping electrodes 66,68 that can be used to record cardiac electrical signals, and in some cases also the delivery of electrical signals to the patient. In some embodiments, the electrodes 66,68 can also be used to facilitate position tracking of the catheter 54 using a position tracking system.

Figure 3:
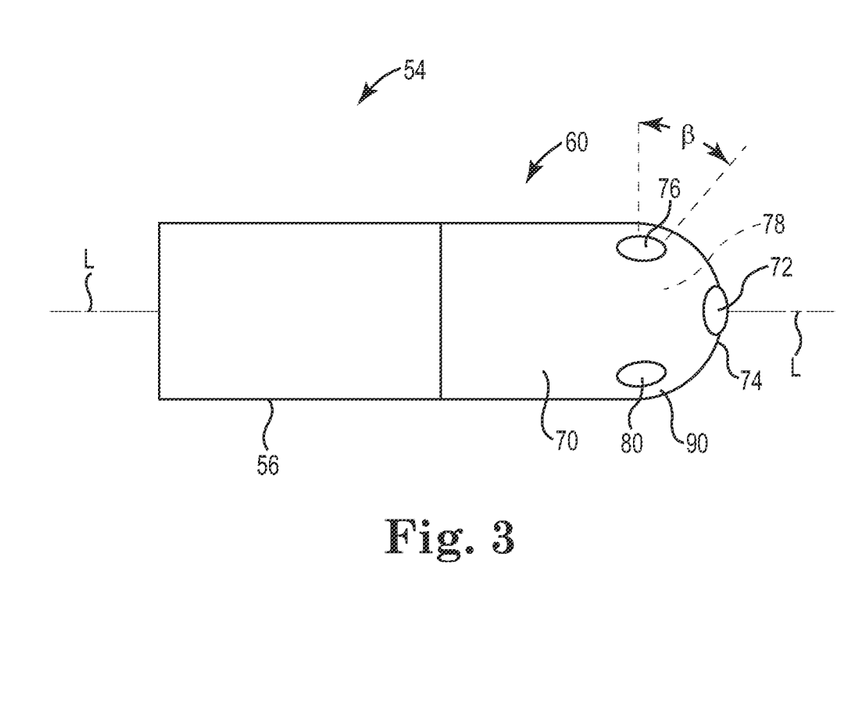
FIG. 3 is a schematic view showing the distal tip section of FIG. 2 in greater detail.

FIG. 3 is a schematic view showing the distal tip section 60 of the probe 54 in greater detail. As can be further seen in FIG. 3, the distal tip section 60 of the probe 54 includes an RF ablation electrode 70 and a plurality of ultrasonic imaging sensors 72, 74, 76, 78. In some embodiments, the RF ablation electrode 70 comprises a conductive material such as platinum, which in addition to serving as an electrode for providing ablation therapy, may also be used as a fluoroscopic marker to determine the location of the distal tip section 60 within the body using fluoroscopy.

In the embodiment shown, the ultrasonic imaging probe 54 includes a distal ultrasonic imaging sensor 72 located at a distal end 74 of the probe 54. The ultrasonic sensor 72 is configured to transmit and receive ultrasonic waves primarily in a forward direction away from the distal end 74 of the probe 54. A second set of ultrasonic imaging sensors 76, 78, 80 located on a curved portion of the distal tip section 60 proximal to the distal-facing ultrasonic imaging sensor 74, in turn, are configured to transmit and receive ultrasonic waves both laterally and in a forward direction away from the distal end 74 of the probe 54. In some embodiments, the ultrasonic sensors 72, 76, 78, 80 each comprise piezoelectric transducers formed of a polymer such as PVDF or a piezoceramic material such as PZT, and are inset within an exposed portion of the RF ablation electrode 70. A number of leads (not shown) extending through the interior space of the probe 54 connect the ultrasonic sensors 72, 76, 78, 80 to the ultrasonic imaging module 18.

During ultrasonic imagining, each of the ultrasonic sensors 72, 76, 78, 80 are configured to operate in alternating pulsing and sensing modes. When excited electrically in the pulsing mode, the ultrasonic sensors 72, 76, 78, 80 generate pressure waves which travel through the electrode 70 and into the surrounding environment. In the sensing mode, the ultrasonic sensors 72, 76, 78, 80 each produce an electrical signal as a result of receiving acoustic waves reflected back to the sensors 72, 76, 78, 80, which are then processed and displayed on the display monitor 50 of the user interface 20. These reflections are generated by the acoustic waves traveling through changes in density in the surrounding environment being imaged.

Figure 4:
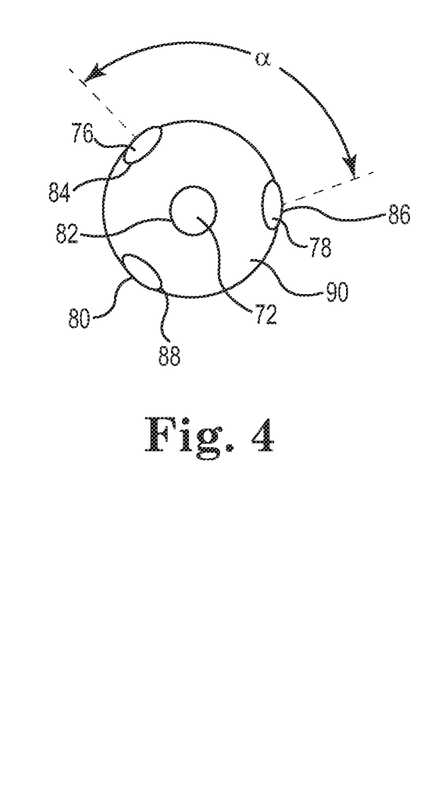
FIG. 4 is an end view showing the distal tip section of FIG. 2 in greater detail.

FIG. 4 is an end view showing the distal tip section 60 of FIG. 2 in greater detail. As can be further seen in FIG. 4, and in some embodiments, the ultrasonic imaging probe 54 includes three ultrasonic sensors 76, 78, 80 equally spaced at an angle α of 120° about the circumference of the distal tip section 60 at a location proximal to the distal ultrasonic sensor 72. Although three ultrasonic sensors 76, 78, 80 are shown in the embodiment of FIG. 4, a greater or lesser number of ultrasonic sensors may be employed. By way of example and not limitation, four ultrasonic sensors may be disposed at equidistant angles α of 90° about the circumference of the distal tip section 60 at a location proximal to the distal ultrasonic sensor 72. During imaging, the use of multiple ultrasonic sensors 76, 78, 80 spaced about the circumference of the distal tip section 60 ensures that at least one of the sensors 76, 78, 80 is in close proximity to the target tissue irrespective of the tip orientation relative to the target tissue. Such configuration also permits the physician to easily visualize the target tissue without having to rotate the probe 54 once the probe 54 is in contact with the tissue. In other embodiments, the location and relative position(s) of each ultrasonic sensor 72, 76, 78, 80 can vary from that shown in FIG. 4.

In some embodiments, an acoustically transparent window or aperture 82, 84, 86, 88 within the electrode 70 facilitates the transmission of ultrasonic waves from the ultrasonic sensors 72, 76, 78, 80 into the surrounding anatomy. In some embodiments, an acoustic coupling fluid within the interior space of the distal tip section 60 serves to couple the acoustic energy transmitted and received via the ultrasonic sensors 72, 76, 78, 80 to the anatomy surrounding the probe 54.

In certain embodiments, and as further shown in FIGS. 3 and 4, each of the proximally-positioned ultrasonic sensors 76, 78, 80 may be located on a curved portion 82 of the ablation electrode 72, and are oriented such that the ultrasonic waves are transmitted at a slightly forward angle β of between about 10° to about 60° relative to a line perpendicular to the longitudinal axis L of the probe 54. During imaging, the off-set orientation of the proximally-positioned ultrasonic sensors 76, 78, 80 directs the ultrasonic waves in a slight forward direction, allowing the physician to better view anatomy and objects that are located at or near the distal end 74.

Figure 5:
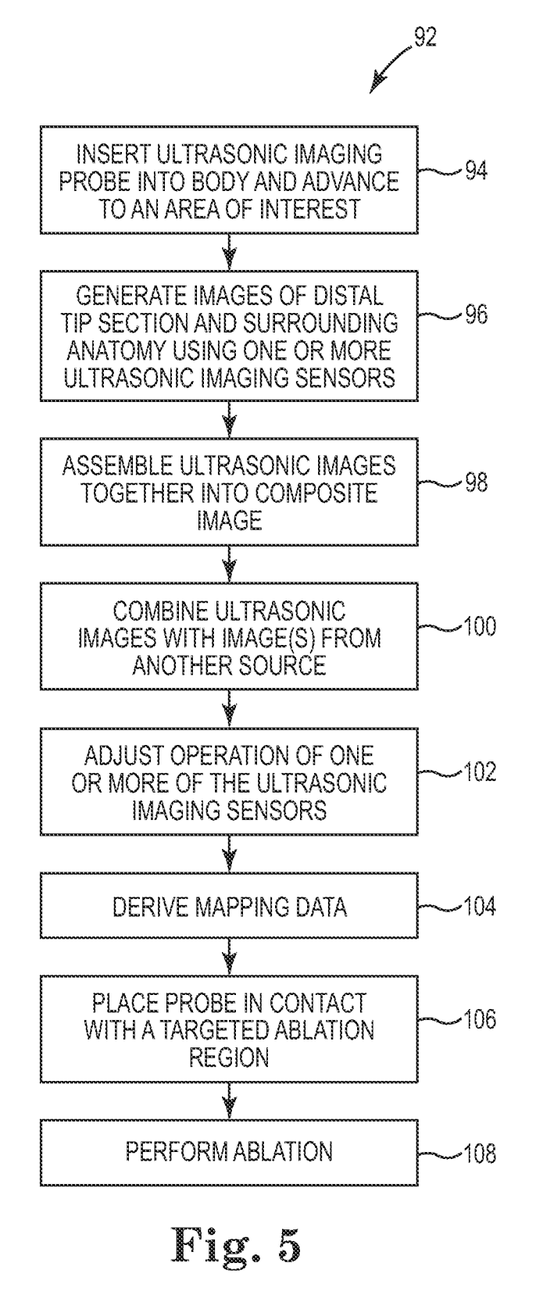
FIG. 5 is a flow diagram showing an illustrative process for visualizing anatomical structures within the body using the ultrasonic imaging system of FIG. 1.

FIG. 5 is a flow diagram showing an illustrative process 92 for visualizing anatomical structures within the body using a combined ablation and ultrasonic imaging probe. FIG. 5 may represent, for example, several exemplary steps that can be used during an ablation procedure to visualize a target ablation site (e.g., myocardial tissue) using the ultrasonic imaging probe 54 of FIG. 2 with the imaging system 10 of FIG. 1.

The process 92 may begin generally at block 94, in which the ultrasonic imaging probe 54 is inserted into the body and advanced intravascularly to an area of interest within the body. In certain electrophysiology procedures, for example, the probe 54 may be inserted into the body via an artery or vein (e.g., the femoral artery) and advanced through the body under fluoroscopic guidance to an area of interest such as the fossa ovalis of the right atrium.

With the ultrasonic imaging probe 54 positioned at the area of interest, the physician may activate the ultrasonic imaging module 18 to generate images of the distal tip section 60 and the surrounding anatomy using one or more of the ultrasonic sensors 72, 76, 78, 80 (block 96). In certain embodiments, each of the ultrasonic sensors are activated continuously and simultaneously, generating multiple, simultaneous images. In other embodiments, the ultrasonic imaging module 18 may selectively activate the ultrasonic sensors in a sequence or pattern, generating multiple images each at a slightly different time.

The images received from each of the ultrasonic sensors can be assembled together into a composite image that can be displayed on a display screen, allowing the physician to quickly ascertain the location of the ablation electrode relative to the target tissue (block 98). In one embodiment, each of the images from the ultrasonic sensors can be used to generate a number of B-mode acoustic images of the area of interest. An example view showing a number of ultrasonic images that can be displayed on a display screen is further shown and described with respect to FIG. 7. In certain embodiments, the ultrasonic images can be combined with images from a fluoroscope, CT-scan, MRI-scan, and/or other source to obtain a composite image (block 100).

Prior to or during ablation, the operation of one or more of the ultrasonic sensors can be adjusted to the specific imaging/detection distance required for the specific application (block 102). For cardiac ablation procedures, for example, the ultrasonic imaging module 18 can be configured to adjust the drive frequency of the ultrasonic drive signals to generate ultrasonic waves that penetrate a distance of between about 2 millimeters to 7 millimeters, and more specifically, about 5 millimeters into the tissue, which is the penetration depth typically needed to visualize and asses the formation of lesions in cardiac tissue. In some embodiments, the ultrasonic imaging module 18 can adjust the operating characteristics of each ultrasonic sensor 72, 76, 78, 80 automatically based on a database of ablation procedure scenarios pre-programmed within the imaging module 18.

As the probe 54 is moved around within the heart under direct visualization using the imaging module 18, the therapy module 16 can be operated to record electrical activity within the heart and derive mapping data (block 104). If an aberrant region is identified via the mapping processor 30, the distal tip section 60 of the probe 54 can be placed into contact with the targeted ablation region (block 106). In some procedures, the images produced by the ultrasonic sensors 72, 76, 78, 80 can be used to confirm whether the probe 54 is in direct contact with the tissue to be treated. Once in position, the RF generator 24 is then operated to begin ablating the tissue (block 108). If necessary, the physician may readjust the positioning of the probe 54 until the ablation is complete. The process can then be performed for any additional target tissue sites that are identified.

FIG. 6 is a view showing an example screen 110 that can be used to display ultrasonic images generated using the ultrasonic imaging probe 54 of FIG. 2 and the user interface 20 of FIG. 1. In the embodiment of FIG. 6, the display screen 98 includes a number of image panes 112, 114, 116, 118 each corresponding to a separate image generated by one of the ultrasonic sensors 72, 76, 78, 80. In certain embodiments, and as shown, the image panes 112, 114, 116, 118 are arranged side-by-side with a first image pane 112 representing a B-mode ultrasonic image generating with the distal ultrasonic sensor 72, and a series of three image panes 114, 116, 118 that may be used to display a separate B-mode ultrasonic image generated by a corresponding one of the ultrasonic sensors 76, 78, 80 located on the probe 54 proximal to the distal ultrasonic sensor 72. A series of labels 120, 122, 124, 126 located adjacent to each image pane 112, 114, 116, 118 provides the physician with information regarding which ultrasonic sensor on the probe 54 corresponds to the image. Label "T" on the display screen 110, for example, may represent that the distal tip transducer 72 on the probe 54 whereas labels "1," "2," and "3" may represent ultrasonic sensors 76, 78, and 80, respectively.

A set of reference lines 128 located on each pane 112, 114, 116, 118 of the display screen 110 provide information regarding the depth at which the image is taken relative to the ultrasonic sensor 72, 76, 78, 80. For cardiac ablation procedures, for example, a set of reference numbers "1 mm," "2 mm," "3 mm," "4 mm," "5 mm" may be located adjacent to each image pane 112, 114, 116, 118, providing the physician with information regarding the depth at which the ultrasonic image was taken.

The number of image panes 112, 114, 116, 118 may vary depending on the number of ultrasonic sensors 72, 76, 78, 80 present on the probe 54. In those embodiments in which the ultrasonic sensors 72, 76, 78, 80 are sequentially timed during each cycle, the image panes 112, 114, 116, 118 may be arranged such that the first image taken during each cycle (e.g., from the distal tip sensor 72) is located on the left-hand side of the display screen 110, and each successive image taken during an imaging cycle is displayed time-wise from left to right on the display screen 110.

FIG. 7 is a view showing an example of a number of B-mode ultrasound images generated on the display monitor screen 110 of FIG. 6. FIG. 7 may represent, for example, a number of ultrasonic images taken with the ultrasonic imaging probe 54 of FIG. 2 during a cardiac ablation procedure in or near a patient's heart.

In the example screen 110 shown in FIG. 7, a first B-mode image 130 in the first image pane 112 is displayed, indicating the presence of bodily tissue located at a depth of approximately 1.5 millimeters away from the distal tip ultrasonic sensor 72, and extending to a depth of approximately 2.0 millimeters. The lower portion of the image 130 represents the location at which the distal end 74 of the ablation electrode 70 contacts the bodily tissue, and may be demarcated on the screen 110 by highlighting, shading, or other visual feature. An upper portion of the image 130, in turn, can be used by the physician to gauge the depth of the anatomical structure, allowing the physician to quickly ascertain what anatomical structure is being imaged.

In the example shown, two distinct B-mode ultrasonic images 132, 134 are displayed on a second image pane 114, indicating the presence of multiple anatomical structures located in the acoustic path of one of the ultrasonic sensors (e.g., sensor 76). A first ultrasonic image 132 located on the image pane 114 may represent, for example, the presence of body tissue (e.g., a first vessel) immediately adjacent to the ablation electrode 70 at the location of ultrasonic sensor 76. A second ultrasonic image 134 located on the image pane 114, in turn, may represent the presence of a second anatomical structure feature (e.g., a second vessel) located further away from the ablation electrode 70 in the path of the ultrasonic sensor 76. The same anatomical structure may also appear on another B-mode ultrasonic image 136 displayed on a third image pane 116.

From each of the images 130, 132, 134, 136, the physician can quickly and easily determine the orientation of the distal tip section 60 relative to the target ablation area without having to rotate the probe 54 within the body, and without the use of position tracking sensors. For example, the presence of the ultrasonic image 132 from about 0 millimeters to about 2 millimeters on image pane 114 indicates that a side of the ablation electrode 70 is in direct contact with the body tissue, and is aligned closest to ultrasonic sensor 76. From this information, the physician can quickly determine the location of the tissue relative to the ablation electrode 70, and can perform the ablation procedure under direct visualization using the ultrasound images.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A combined ablation and ultrasound imaging probe for insertion within a body, the probe comprising:
 a housing having a proximal section and a distal tip section;
 an ablation electrode located at the distal tip section, the ablation electrode comprising a metal shell, the metal shell having a distal-facing aperture formed through the metal shell and a plurality of lateral-facing apertures formed through the metal shell and located proximal of the distal facing aperture, the plurality of lateral-facing apertures arrayed around a circumference of the metal shell;
 a first ultrasonic imaging sensor located at least partially within the metal shell, the first ultrasonic imaging sensor configured to transmit acoustic waves in a first direction through the distal-facing aperture, the first direction orientated primarily distally away from the distal tip section; and
 a plurality of second ultrasonic imaging sensors located at least partially within the metal shell and proximal to the first ultrasonic imaging sensor, the plurality of second ultrasonic imaging sensors arrayed about the circumference of the metal shell and configured to transmit acoustic waves through the plurality of lateral-facing apertures in a plurality of second directions, respectively, the plurality of second directions orientated laterally away from the distal tip section and different from the first direction.

2. The probe of claim 1, wherein the ablation electrode comprises an RF ablation electrode.

3. The probe of claim 1, wherein each of the first and second ultrasonic imaging sensors are disposed entirely within the distal tip section.

4. The probe of claim 1, wherein the plurality of apertures are evenly spaced about the circumference of the metal shell.

5. The probe of claim 1, wherein each of the second ultrasonic imaging sensors are located along a curved portion of the metal shell.

6. The probe of claim 5, wherein each of the second ultrasonic imaging sensors are configured to transmit acoustic waves at an angle of between about 10° to about 60° relative to a line perpendicular to a longitudinal axis of the housing.

7. The probe of claim 1, wherein the plurality of second ultrasonic imaging sensors consists of three ultrasonic imaging sensors evenly arrayed at angles of 120° about the circumference of the metal shell.

8. The probe of claim 1, wherein the plurality of second ultrasonic imaging sensors consists of four ultrasonic imaging sensors evenly arrayed at angles of 90° about the circumference of the metal shell.

9. The probe of claim 1, wherein the probe further includes at least one mapping electrode.

10. An imaging and ablation probe for insertion within a body, the probe comprising:
   a catheter having a distal tip section;
   an ablation electrode located at the distal tip section, the electrode formed from an electrically conductive metal, the electrode having a distal aperture and a plurality of side apertures, all of said apertures formed through the electrically conductive metal of the electrode, the distal aperture distal with respect to each of the plurality of side apertures, the plurality of side apertures arrayed around a circumference of the electrode;
   a first ultrasonic imaging sensor located within the electrode and configured to transmit acoustic waves through the distal aperture in a first direction, the first direction orientated primarily distally away from the electrode; and
   a plurality of second ultrasonic imaging sensors within the electrode and configured to transmit acoustic waves, the plurality of second ultrasonic imaging sensors directly axially aligned with the plurality of side apertures, respectively, to transmit the transmit acoustic waves through the plurality of side apertures in a plurality of second directions, respectively, the plurality of second directions orientated laterally with respect to a longitudinal axis of the distal tip section.

11. The probe of claim 10, wherein the electrode comprises an RF ablation electrode.

12. The probe of claim 10, wherein each of the first and second ultrasonic imaging sensors are disposed entirely within the electrode.

13. The probe of claim 10, wherein the plurality of side apertures are evenly spaced about the circumference of the electrode.

14. The probe of claim 10, wherein each of the second ultrasonic imaging sensors are located along a curved portion of the electrode.

15. The probe of claim 14, wherein each of the second ultrasonic imaging sensors is configured to transmit acoustic waves at an angle of between about 10° to about 60° relative to a line perpendicular to the longitudinal axis of the distal tip section.

16. The probe of claim 10, wherein the plurality of side apertures consists of three apertures evenly spaced around the circumference of the electrode at angles of 120°.

17. The probe of claim 10, wherein the plurality of side apertures consists of four apertures evenly spaced around the circumference of the electrode at angles of 90°.

18. An imaging and ablation probe for insertion within a body, the probe comprising:
   a catheter having a distal tip section;
   an RF ablation electrode located at the distal tip section, the RF ablation electrode formed from an electrically conductive metal, the electrode having a distal aperture and a plurality of side apertures, all of said apertures formed through the electrically conductive metal of the electrode, the distal aperture located distal with respect to each of the plurality of side apertures, the plurality of side apertures evenly spaced around a circumference of the electrode;
   a first ultrasonic imaging sensor inset within the electrode and configured to transmit acoustic waves in a first direction through the distal aperture, the first direction orientated primarily distally from the electrode; and
   a plurality of second ultrasonic imaging sensors inset within the electrode and each directly aimed in one of a plurality of different directions, respectively, and configured to transmit acoustic waves through the plurality of side apertures in the plurality of second directions, respectively, the plurality of second directions laterally directed with respect to the electrode and respectively different from each other and the first direction.

* * * * *